US00RE37154E

(19) United States
(12) Reissued Patent
Nomura et al.

(10) Patent Number: US RE37,154 E
(45) **Date of Reissued Patent: *May 1, 2001**

(54) METHOD OF MANUFACTURING DISPOSABLE UNDERPANTS BY APPLYING ANNULAR ADHESIVE ZONES TO THE BACKSHEET AND TOP SHEET FOR RETAINING ELASTIC FOR LEG HOLES

(75) Inventors: Hironori Nomura, Iyomishima; Taiji Shimakawa, Kanonji; Sadanori Matsura, Kanonji; Hiroki Yamamoto, Kawanoe; Hirofumi Ohnishi, Iyomishima, all of (JP)

(73) Assignee: Uni-Charm Corporation, Ehime-ken (JP)

( * ) Notice: This patent issued on a continued prosecution application filed under 37 CFR 1.53(d), and is subject to the twenty year patent term provisions of 35 U.S.C. 154(a)(2).

(21) Appl. No.: 08/629,323

(22) Filed: Apr. 8, 1996

Related U.S. Patent Documents

Reissue of:
(64) Patent No.: 5,147,487
Issued: Sep. 15, 1992
Appl. No.: 07/745,708
Filed: Aug. 16, 1991

U.S. Applications:

(63) Continuation of application No. 08/305,534, filed on Sep. 14, 1994, now abandoned, which is a continuation of application No. 07/545,621, filed on Jun. 29, 1990, now abandoned.

(30) Foreign Application Priority Data

Jun. 29, 1989 (JP) ..... 1-167224

(51) Int. Cl.[7] ..... B32B 31/10; A61F 13/15

(52) U.S. Cl. ..... 156/164; 156/161; 156/204; 156/229; 156/267; 156/269; 156/291; 156/494

(58) Field of Search ..... 156/161, 164, 156/163, 291, 229, 494, 267, 269, 211, 227; 2/400–402; 604/385.1, 385.2, 358; 427/208.6

(56) References Cited

U.S. PATENT DOCUMENTS

| | | | | |
|---|---|---|---|---|
| 3,560,292 | * | 2/1971 | Butter | 156/229 |
| 3,828,367 | * | 8/1974 | Bourgeois | 156/164 X |
| 4,205,679 | * | 6/1980 | Repke et al. | 604/385.2 X |
| 4,284,454 | * | 8/1981 | Joa | 156/229 X |
| 4,417,935 | * | 11/1983 | Spencer | 156/229 X |

(List continued on next page.)

FOREIGN PATENT DOCUMENTS

| | | | | |
|---|---|---|---|---|
| 0048011 | * | 3/1982 | (EP) | 156/164 |
| 2169489 | * | 7/1986 | (GB) | 604/358 |
| 2235125 | * | 2/1991 | (GB) . | |
| 57-77304 | * | 5/1982 | (JP) . | |
| 57-117602 | * | 7/1982 | (JP) . | |

OTHER PUBLICATIONS

Gibilisco, Stan, "The Concise Illustrated Dictionary of Science and Technology," McGraw–Hill, Inc, 1993, p. 262.*
Walker, Peter MB, "Dictionary of Science and Technology," Larousse, 1995, p. 639.*

*Primary Examiner*—Jeff H. Aftergut
(74) *Attorney, Agent, or Firm*—Lowe Hauptman Gilman & Berner, LLP

(57) ABSTRACT

Here is disclosed a method for manufacturing individual disposable underpants provided around a waist line and a pair of leg-holes with elastic members from two continuous webs and a plurality of continuous elastic members, characterized by that the webs are applied on predetermined locations with adhesive so that the elastic members can be reliably held on the webs although the elastic members must be forcibly curved when the elastic members are bonded between the webs with use of adhesive.

24 Claims, 8 Drawing Sheets

U.S. PATENT DOCUMENTS 4,464,217 * 8/1984 Dickover et al. ..... 156/164
4,563,185 * 1/1986 Reiter ..... 604/385.2
4,585,447 * 4/1986 Karami ..... 604/385.2
4,646,362 * 3/1987 Heran et al. ..... 604/385.2 X
4,650,530 * 3/1987 Mahoney et al. ..... 156/204 X
4,764,234 * 8/1988 Smits et al. ..... 156/164
4,795,451 * 1/1989 Buckley ..... 604/385.2
4,801,345 * 1/1989 Dussaud et al. ..... 156/164
4,842,666 * 6/1989 Werenicz ..... 156/161
4,849,049 * 7/1989 Colton ..... 156/291
4,891,249 * 1/1990 McIntyre ..... 156/301 X
4,909,804 * 3/1990 Douglas, Sr. ..... 604/385.2
4,915,767 * 4/1990 Rajala et al. ..... 156/161 X
4,938,821 * 7/1990 Soderlund et al. ..... 156/164 X
4,940,464 * 7/1990 Van Gonpel et al. ..... 604/385.2 X

* cited by examiner

METHOD OF MANUFACTURING DISPOSABLE UNDERPANTS BY APPLYING ANNULAR ADHESIVE ZONES TO THE BACKSHEET AND TOP SHEET FOR RETAINING ELASTIC FOR LEG HOLES

Matter enclosed in heavy brackets [ ] appears in the original patent but forms no part of this reissue specification; matter printed in italics indicates the additions made by reissue.

[This is a continuation of application Ser. No. 07/545,621, filed Jun. 29, 1990, now abandoned, and the benefits of 35 USC 120 are claimed relative to it.]

*This application is a continuation of applicaton Ser. No. 08/305,534 filed Sep. 14, 1994 now abandoned, which is a reissue of Ser. No. 07/745,708 filed Aug. 16, 1991, now U.S. Pat. No. 5,147,487 which is a continuation of Ser. No. 07/545,621 filed Jun. 29, 1990, now abandoned.*

BACKGROUND OF THE INVENTION

The present invention generally relates to disposable underpants and, more particularly, to a method for manufacturing such diapers in the form of underpants and infant training shorts.

Various approaches to such underpants or shorts have already been well known from, for example, Japanese Patent Application Disclosure Gazettes Nos. 1982-77304 and 1982-117602. These Gazettes disclose the methods for attachment of the elastic members to the waist-hole and the leg-holes of the underpants, particularly along the curves of the respective leg-holes so as to improve a fitness around the wearer's legs.

In order to ensure that a continuous elastic member can be continuously attached to web at locations to be formed into the waist-hole and the leg-holes, respectively, during continuous manufacturing basic bodies of underpants from said web, it is generally required that such continuous elastic member must be kept stretched at a predetermined ratio when it is attached to said web at said locations with use of suitable adhesive. Turning to the above-referred prior art, they disclose the procedure in which the continuous elastic member carrying said adhesive previously applied thereon is attached to the continous web.

Generally, when the elastic member is attached to the web while the elastic member is curved according to the curve, for example, of the leg-hole, the elastic member tends to restore its initial rectilinearity, due to its contractility, and sometimes to be attached to the web at a location deviating from the proper location at which the elastic member should be attached to the web.

Such undesirable deviation or shift of the elastic member may occur also in the above-referred prior art because, according to such prior art, the elastic member carrying adhesive previously applied thereon must be attached to fibrous nonwoven fabric having its surface usually less smooth than that of plastic film and an adhesive effect is correspondingly low. This necessarily makes any high speed handling difficult. When the elastic member is continuously attached to the web while the elastic member is curved so as to follow the curve of the leg-hole under control of traverse means, a certain quantity of adhesive is inevitably transferred onto the traverse means as the elastic member carrying adhesive previously applied thereon passes by the traverse means. Thus, the elastic member is peeled off or displaced to deteriorate the adhesive effect and inconveniently requires frequent cleaning of the traverse means particularly at the portion thereof where the elastic member passes by.

Accordingly, it is a primary object of the invention to provide a method for manufacturing disposable diapers allowing the above-mentioned problem conventionally encountered by the prior art to be solved by attaching the elastic member to the web along an annular adhesive zone in each location to be formed into a leg-hole wherein said annular adhesive zone is defined by a strip of adhesive having a width larger than that of the elastic member.

SUMMARY OF THE INVENTION

The object set forth above is achieved, in accordance with the invention, by a method comprising steps of: providing annular adhesive zones centrally on one side of a first continuous web intermittently along the length thereof; introducing first and second continuous elastic members having a width narrower than that of a strip of adhesive defining said annular adhesive zones toward the central area on said one side of said first continuous web so that said first continuous elastic member is laid to bond along substantially a half of said annular adhesive zone while said second continuous elastic member is laid to bond along substantially the remainder half of said annular adhesive zone; providing ribbon-like adhesive zones extending along lateral edges on one side of at least one of said first continuous web and a second continuous web; introducing a third group of continuous elastic members between the mutually opposed sides of said first continuous web and said second continuous web along the respective lateral edges so as to be bonded between these webs along said ribbon-like adhesive zones; bonding said first and second continuous webs together along said respective one sides to form a continuous combined web; folding said continuous combines web into two along a longitudinally central line; cutting off portions of said continuous combined web encircled within respective annular zones each comprising said annular adhesive zone, said first and second elastic members bonded to the web along said annular adhesive zone, after forming or folding double said combined web to form cutouts for leg-holes; providing linear seal zones extending transversely of said twofold continuous combined web centrally through said respective cutouts for the leg-holes to one lateral edge of said combined web corresponding to the waist line so as to form continuous series of underpants; and cutting said continuous series of underpants along each of said linear seal zones transversely of said continuous series of underpants so that each of said linear seal zones is divided in two longitudinally of said continuous combined web and thereby obtaining individual underpants.

In a preferred embodiment, there are provided on the one side of the second continuous web additional annular adhesive zones repectively identical to and associated with said first-mentioned annular adhesive zones so that said first and second continuous elastic members are sandwiched between these mutually adjacent annular adhesive zones.

To manufacture underpants containing therein an absorbent core, an absorbent core is interposed between each pair of said adjacent annular adhesive zones prior to bonding said first and second continuous webs to each other.

According to the present invention, as has been described hereinabove, there are provided the annular adhesive zones defined by strips of adhesive having a width larger than that of the continuous elastic members intermittently along the length of said web and the continuous elastic members for the leg-holes are attached to the web along these annular adhesive zones. With a consequence, the continuous elastic members can be safely and reliably held on the continuous web without significant displacement or shift of the continuous elastic members from the associated annular adhesive zones even if the continuous web is of fibrous nonwoven fabric. Such effect is enhanced when another continuous web is provided with the annular adhesive zones in alignment with the previously mentioned annular adhesive zones, respectively, so that the continuous elastic members may be sandwiched between the respective sets of mutually facing annular adhesive zones.

Finally, said annular adhesive zones are provided on the continuous web, instead of applying adhesive directly on said continuous elastic member, so that the problem encoutered by the above-referred prior art adopting said application of adhesive directly on the continuous elastic members may be solved.

PREFERRED EMBODIMENT OF THE INVENTION

An embodiment of the invention will be described in greater detail in reference with the accompanying drawings.

Figure 1:
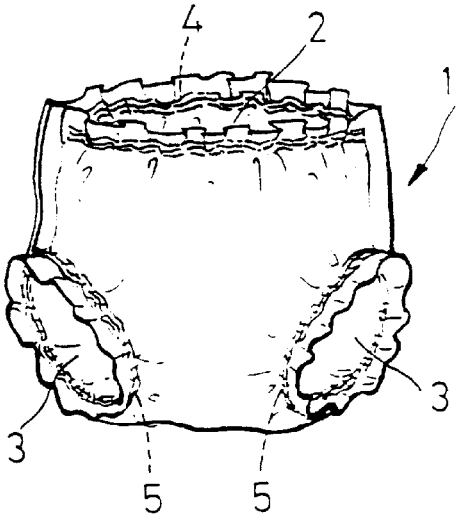
FIG. 1 is a perspective view showing disposable underpants to be manufactured by the method according to the invention as has been completely assembled.

FIG. 1 is a perspective view showing disposable underpants to be manufactured by the method of the invention as has been completely assembled. The underpants 1 include a waist-hole 2, a pair of leg-holes 3 and elastic members 4, 5 adhesively attached to the underpants 1 around these holes so as to form elastic gathers therearound.

Figure 2:
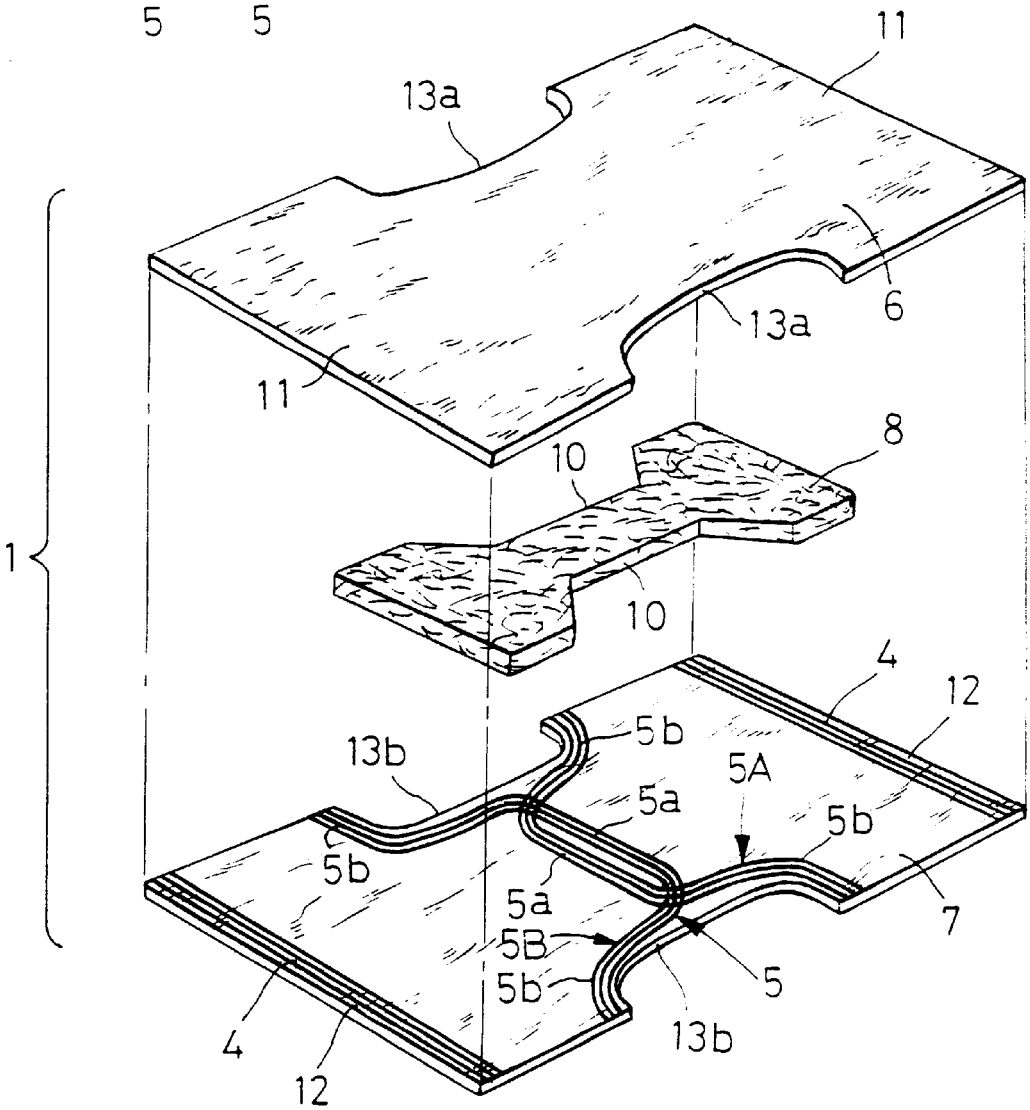
FIG. 2 is an exploded perspective view of said underpants.

FIG. 2 is an exploded perspective view of said underpants. As seen in FIG. 2, the underpants 1 comprise a topsheet 6 and a backsheet 7 respectively made of fibrous nonwoven fabric being elastic both in length and width, a mat-like absorbent core 8 sandwiched between these sheets, and said elastic members 4, 5. The topsheet 6 and the backsheet 7 are respectively provided in opposite sides with notches 13a, 13a and with notches 13, 13b. The core 8 is also provided in opposite sides with notches 10, 10 so as to present so-called sandglass-shape. The core 8 is made primarily of fluffy pulp. The elastic member 4 is bonded in a laterally elastic manner between the topsheet 6 and the backsheet 7 along waist portions 11, 12 thereof with use of adhesive as will be described. The elastic member 5 comprises first and second submembers 5A, 5B which comprise, in turn, three rubber strings having central portions 5a, 5a and opposite side portions 5b, 5b. These rubber strips are secured between the topsheet 6 and the backsheet 7 only at their opposite side portions 5a, 5b.

Figure 3:
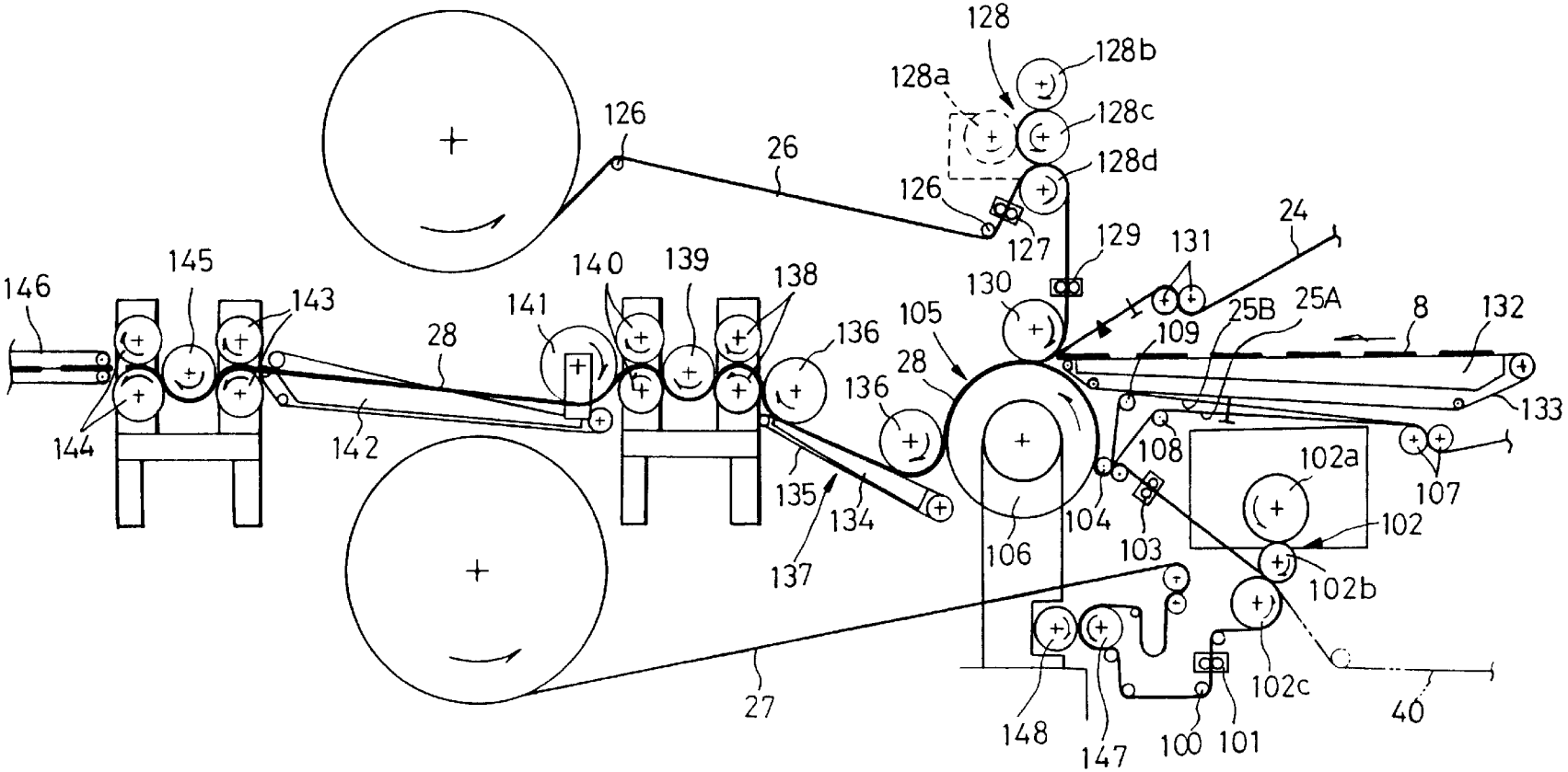
FIG. 3 is a schematic diagram illustrating an apparatus for manufacturing said underpants.

FIG. 3 schematically illustrates an apparatus for manufacturing said underpants. A continuous web 27 as material for said backsheet 7 is guided by a group of guide rollers 100 and a tensioning roller pair 101 adapted to tension said web transversely therof into an adhesive applicator station 102 consisting of rollers 102a, 102b, 102c. At the application station 102, the web 27 is applied centrally thereon with adhesive of hot melt type of provide oval adhesive zones 30a which are slightly elongate transversely of said web 27 and spaced from one another by regular intervals longitudinally of said web 27. The web 27 is then guided by a tensioning roller pair 103 adapted to tension said web 27 transversly thereof and a squeeze roller pair 104 onto a rotable drum 106 in an assembling station 105.

Three continuous elastic members 25A, 25B as said respective elastic submembers 5A, 5B are stretched by a stretching roller pair 107 as they are guided to traverse means 108, 109.

Figure 4A:
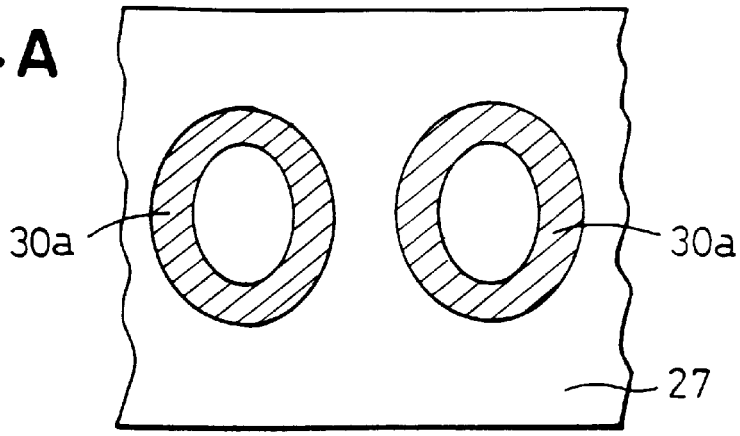
FIG. 4A through 4E and FIGS. 5A through 5C are fragmentary plan views illustrating respective steps for assembly of said underpants.
Figure 4B:
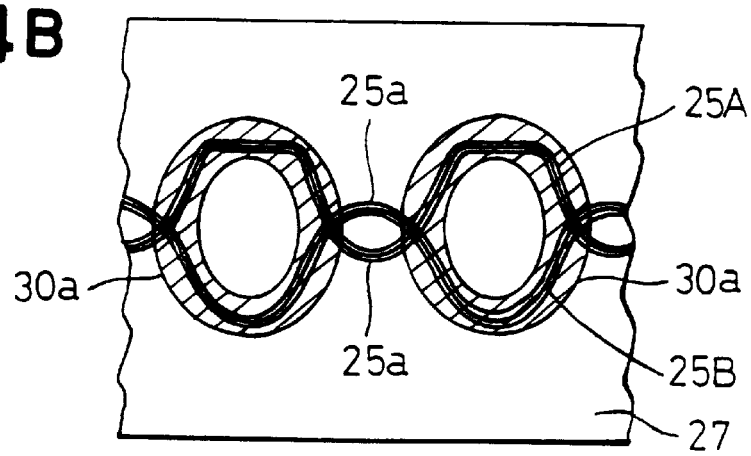
Figure 6:
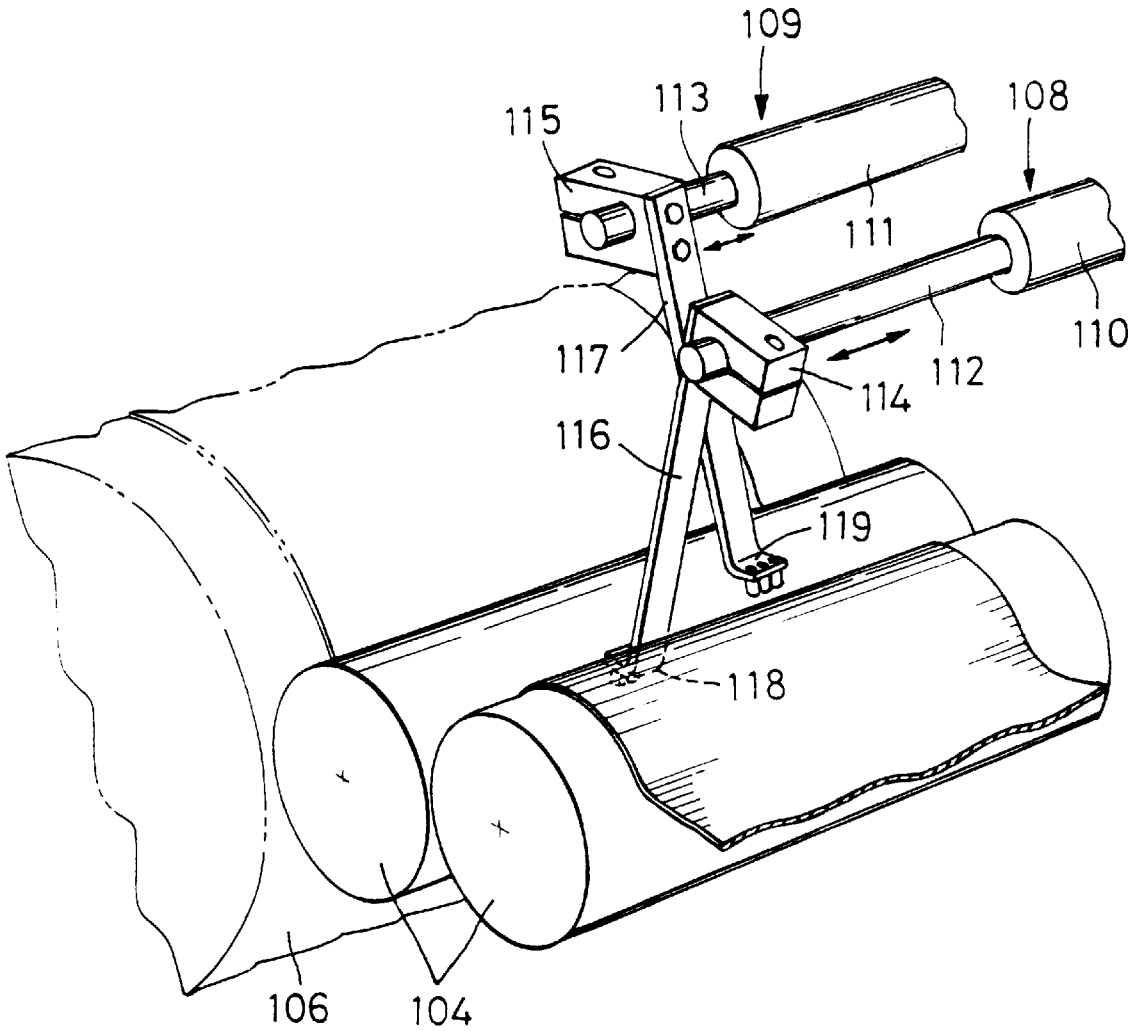
FIG. 6 is a fragmentary perspective view showing, in enlarged scale, traverse means used in said apparatus.
Figure 7:
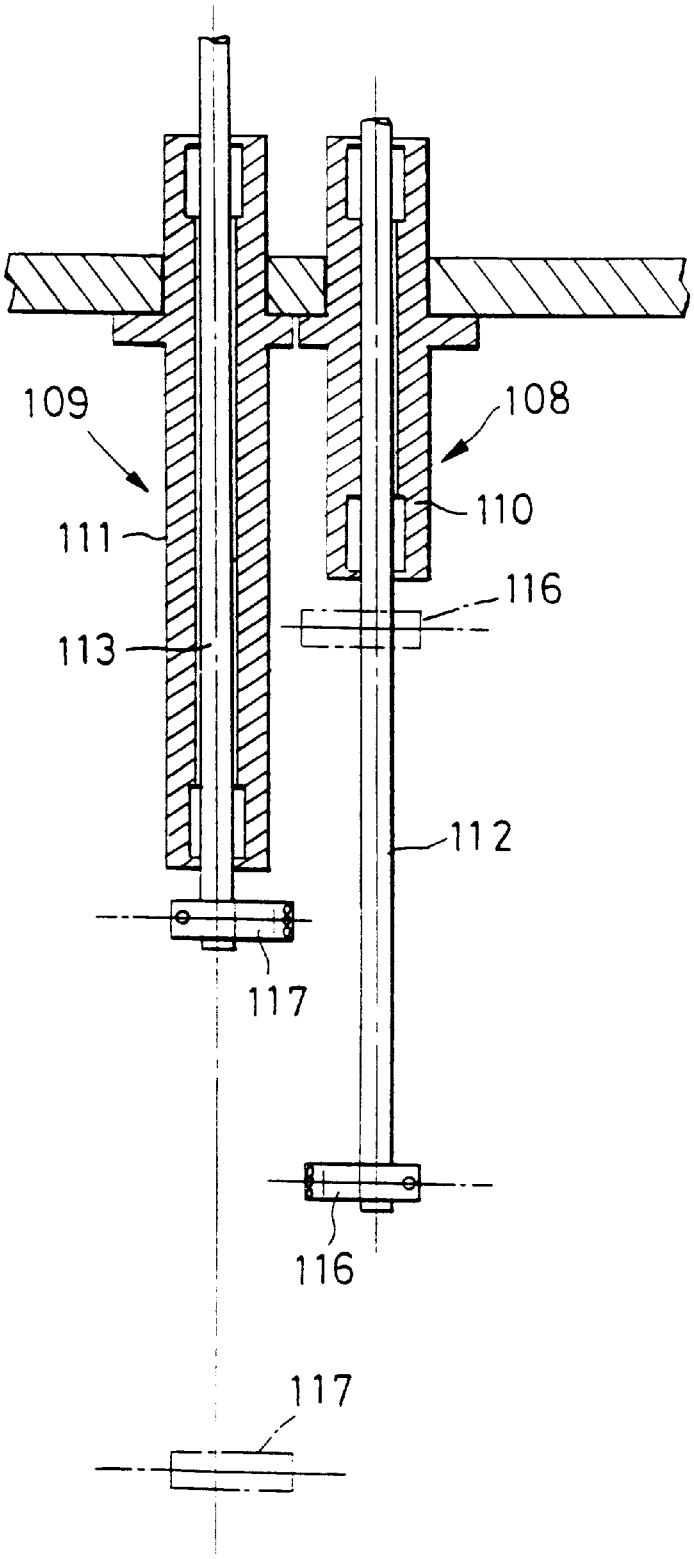
FIG. 7 is a fragmentary sectional view of said traverse means.

FIG. 6 and 7 schematically show, in perspective and sectional views, respectively, arrangement of the traverse means 108, 109. As shown, the traverse means 108, 109 respectively include support cylinders 110, 111 positioned adjacent and in parallel with the squeeze roller pair 104, slidably movable rods 112, 113 inserted into said support cylinders, respectively, and guide rods 116, 117 suspended from support blocks 114, 115 which are, in turn, fixed to forward ends of said slidably movable rods, respectively. Said slidably movable rods 112, 113 are under control of traverse cams (not shown) linked to base ends of these rods 112, 113, respectively. The guide rods 116, 117 are provided in lower ends thereof with guide holes 118, 119 through which said elastic members 25A, 25B are respectively inserted. The lower ends of the guide rods 116, 117 are closely adjacent peripheral surfaces of the squeeze roller pair 104. The slidably movable rods 112, 113 are movable by distances between positions of the respective guide rods 116, 117 indicated by solid lines and positions of said rods 116, 117 indicated by chain lines in FIG. 7 under control of said traverse cams. As the slidably movable rods 112, 113 and, hence, the guide rods 116, 117 are moved under such control, the elastic members 25A, 25B which are finer than the strips of adhesive defining said adhesive zones 30a on the web 27 are laid to bond on said web 27 traveling together with said adhesive zones 30a so that elastic member 25A, 25B follow substantially halves of each pair of adjacent adhesive zones 30a, then intersect each other in the area defined between these adjacent adhesive zones 30a and follow the remainer halves thereof, describing a pair of sine curves, as shown by FIG. 4B.

Figure 8:
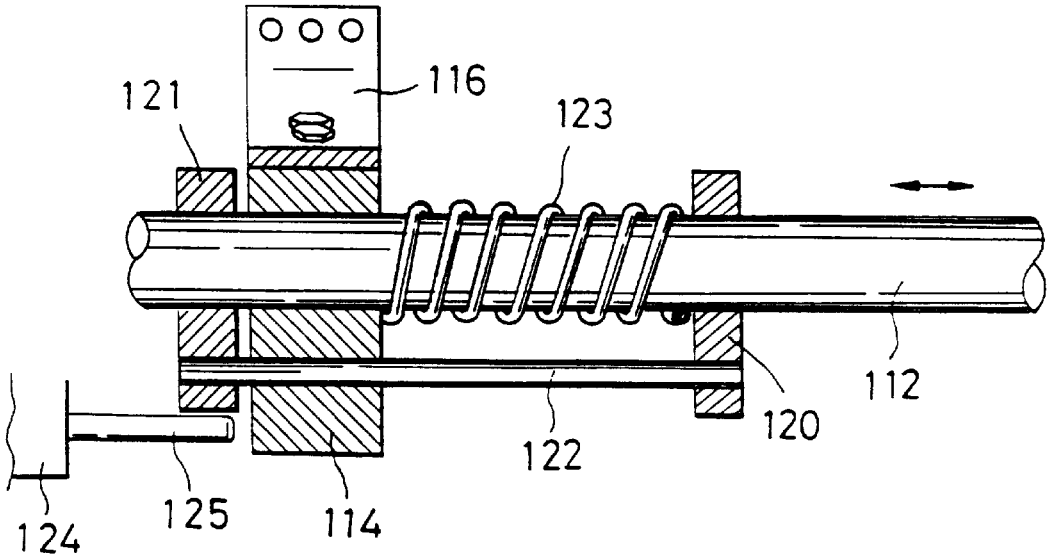
FIG. 8 is a sectional view of a traverse deforming mechanism in said tranverse means.
Figure 9:
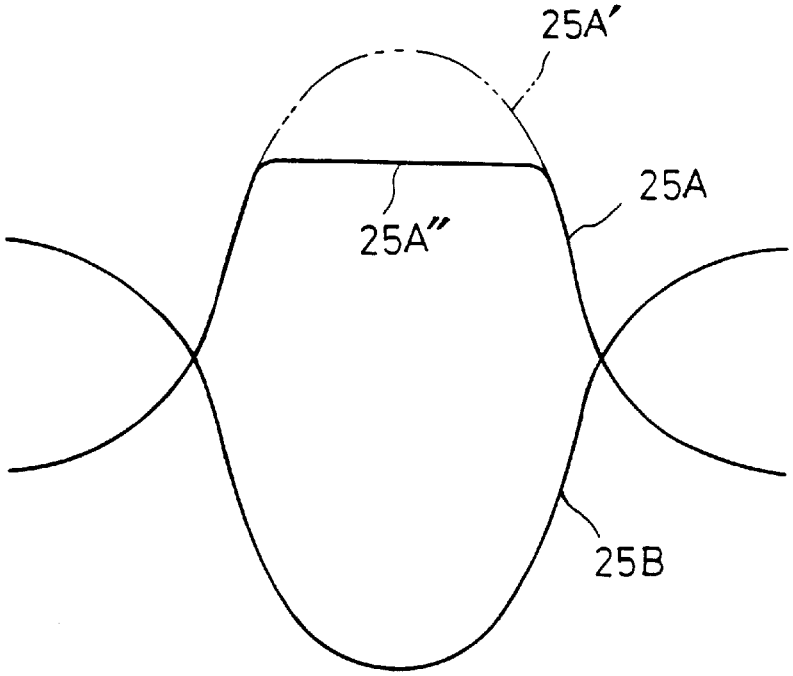
FIG. 9 is a schematic plan view illustrating elastic members under deformation by said traverse deforming mechanism.

FIG. 8 is a fragmentary sectional view showing a mechanism adapted to control movement of the slidably moveable rod 112 and the guide rod 116 and thereby to partially deform the sine curve described by said elastic member 25A, and FIG. 9 is a plan view showing said sine curve thus partially deformed. Referring to FIG. 8, adjacent the forward end of the support cylinder 110 shown in FIG. 6, there are stationarily provided on the slidably movable rod 112 a pair of regulator blocks 120, 121 spaced from each other along the length of said slidably movable rod 112 and a support block 114 is slidably mounted on the portion of the slidably movable rod defined between the regulator blocks 120, 121 as well as on a guide rail 122 extending between said regulator blocks. A coil spring 123 is loaded between the support block 114 and the regulator block 120. A stopper 125 extends from a stationary component 124 so that the stopper 125 may contact an opposed side surface of the support block 114 and thereby limit movement thereof. If the slidably movable rod 112 is not provided with such mechanism, the elastic member 25A would discribed a sine curve having a circular section 25A' as the slidably movable rod 112 and the guide rod 116 are moved whereas, in the case as shown by FIG. 8 in which the slidably movable rod 112 is provided with such mechanism, upon contact of the support block 114 supporting the guide rod 116 with the stopper 125, said sine curve of the elastic member 25A is deformed so as to describe a linear section 25" corresponding to a period during which the guide rod 116 is temporarily stopped by the stopper 125 bearing against the support block 114. Such deformed sine curve of the elastic member 25A is designed in accordance with the configurations of the leg-holes 3 shown in FIG. 1 and the wearer's front crotch in order to improve the fitness.

Figure 4C:
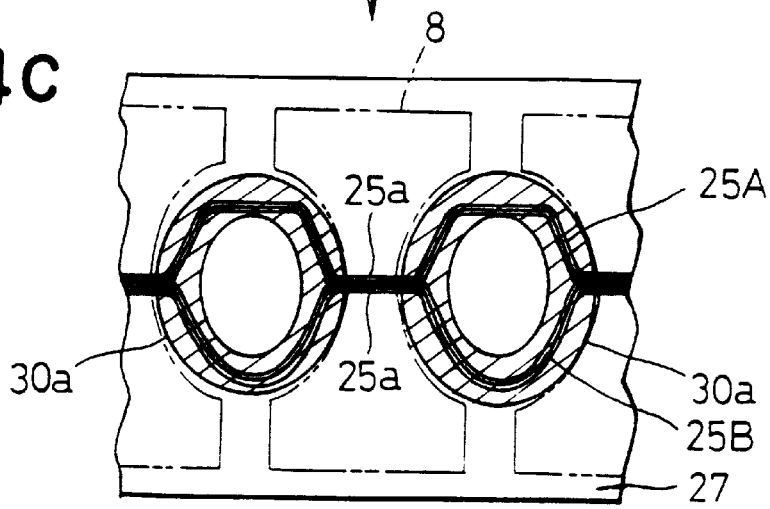

The web 27 including the elastic members 25A, 25B laid thereon in the manner as has been mentioned above is squeezed between the squeeze roller pair 104 and thereby said elastic members are adhesively bonded to said web. On this point, the portions 25a, 25a of the respective elastic members 25A, 25B not lying within the adhesive zones 30a contract to present substantially rectilinear shape, as seen from FIG. 4C.

Figure 4D:
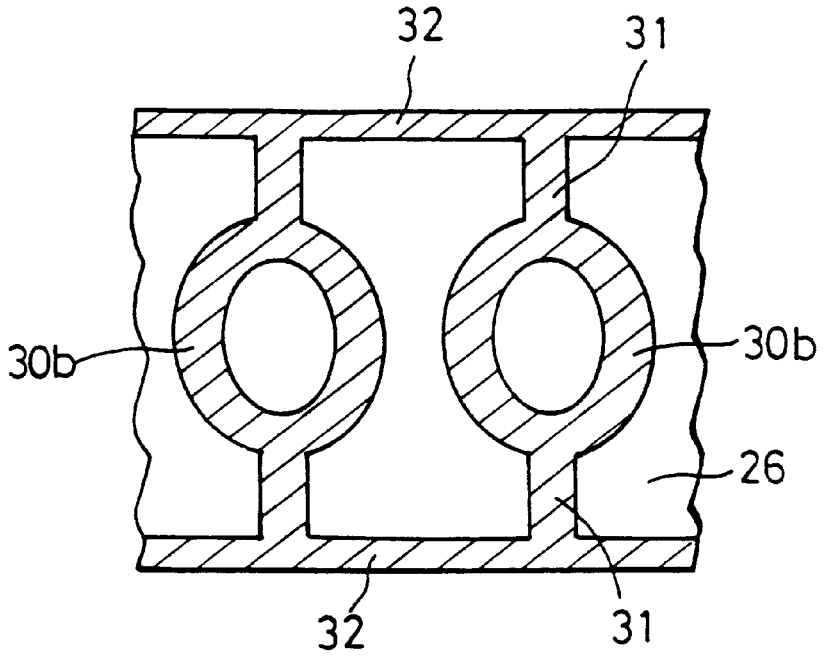

Referring again to FIG. 3, a continuous web 26 as material for said topsheet 6 is guided by a guide roller 126 and a tensioning roller pair 127 adapted to tension said web 26 transversely thereof to an adhesive applicator station 128 comprising rollers 128a, 128b, 128d. At the applicator station 128, the web 26 is applied centrally thereon with hot melt type adhesive to provide oval adhesive zones 30b which are slightly elongate transversely of said web 26, as shown by FIG. 4D. Shape, size and spacing of this adhesive zone 30b are substantially identical to the previously mentioned adhesive zone 30a. Simultaneously, the web 26 is provided with rectilinear adhesive zones 31 extending from opposite sides of said adhesive zone 30b to the adjacent lateral edges of the web 26, respectively, and continuous rectilinear adhesive zones 32 longitudinally extending along the lateral edges of the web 26 by application of hot melt type adhesive occuring at said applicator station. Then, the web 26 is introduced by a tensioning roller pair 129 also adapted to tension the web 26 transversely thereof between the rotatable drum 106 and a pressure roller 130 cooperation with said drum.

Figure 4E:
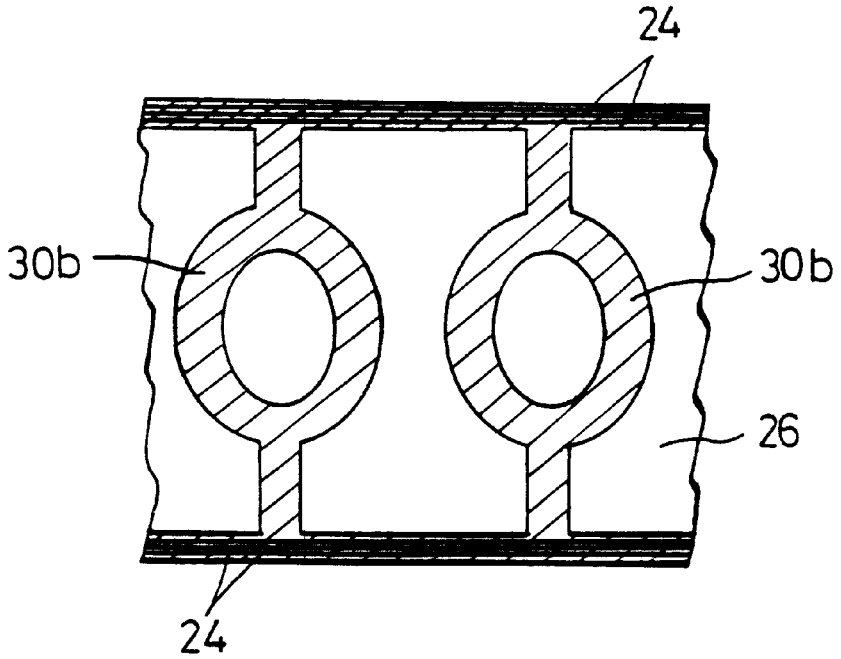

The continuous elastic members 24 as material for said elastic members 4 are stretched to a desired ratio and guided simultaneously by a stretching roller pair 131 so as to be laid and bonded along the adhesive zones 32 formed along the lateral edges of the web 26, as shown by FIG. 4E.

Referring again to FIG. 3, the individual cores 8 previously formed and placed at regular spacings on a porous belt conveyor 133 adapted to be moved over the top of a device 132 having a relatively feeble suction effect and conveyed by the belt conveyor 133 to the assembling station 105. As will be apparent from FIG. 2 and FIG. 4C (as indicated by chain lines), each core 8 presents so-called sandglass shape and located between each pair of adjacent adhesive zones 30a or each pair of adjacent loop portions formed by the elastic members 25A, 25B, respectively, on the web 27. Upon the web 27 carrying the core 8 disposed thereon, the web 26 is placed so that said adhesive zones 30a, 30a are aligned with said adhesive zones 30b, 30b. In this manner, the respective loop portions of said elastic members, 25A, 25B are properly sandwiched between said webs 26, 27 at said adhesive zones 30a, 30b and the elastic members 24 are also properly sandwiched between these webs 26, 27 along their lateral edges. Thus, the webs 26, 27 sandwiching the cores 8 and the elastic members 24, 25A, 25B therebetween are squeezed between the rotatable drum 106 and the pressure roller 130 to form the continuous combined web 28 and simultaneously to fix the cores 8 and the elastic members 24, 25A, 25B within this combined web 28.

Figure 5A:
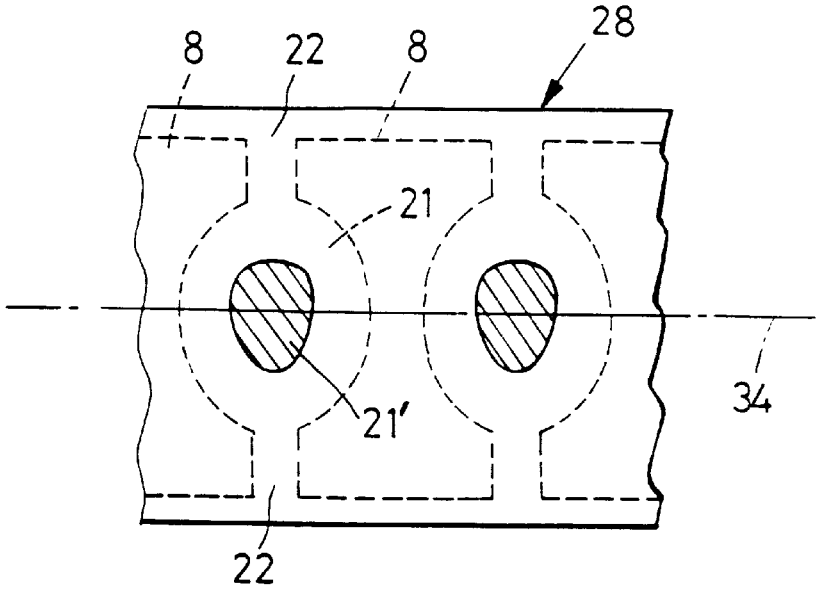

The combined web 28 enclosing the cores 8 therein is then pressed at a press station comprising a belt conveyor 135 traveling on the top of a cradle 134 and pressure rollers 136 and thereafter guided to a heat (or sonic) seal roll pair 138. The combined web 28 is heat sealed by the seal roll pair 138 at oval zones 21 defined by each pair of adjacent cores 8 and rectilinear sections 22 extending from opposite sides of the respective oval zones 21 to the adjacent lateral edges of the combined web 28, respectively, as shown by FIG. 5A. In this case, excessively hardened heat seal is undesirable. It should be understood that this process is not necessarily essential to the invention.

The combined web 28 thus process is now guided by a guide roller 139 to a roll cutter 140 by which a hatched central area 21' of the oval zone 21 is cut out to form the cutout 23 for the leg-hole. The central area 21' comprises portions of the webs 26, 27 lying inside each of the annular zones formed by the adhesive zones 30a, 30b and the elastic members 25A, 25B adhesively bonded therealong.

Figure 5B:
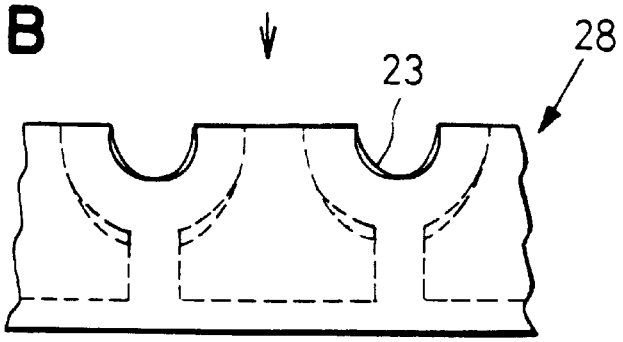
Figure 5C:
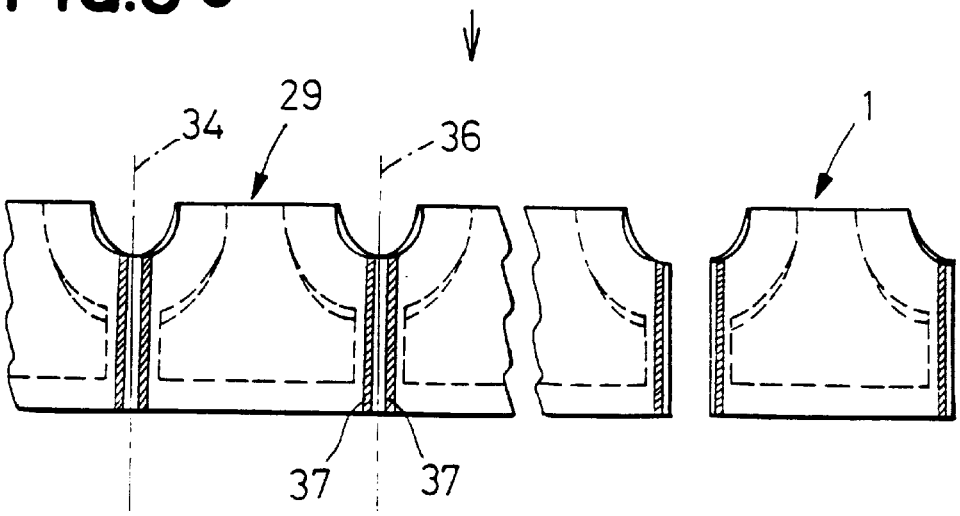

The combined web 28 thus formed with the cutouts 23 is guided by a guide roller 141 to folding means 142 of which detals are not shown. The folding means 142 may be of the arrangement well known in the apparatus for manufacturing disposable diapers, sanitary napkins or the like. The combined web 28 is folded by the folding means 142 along a longitudinally central line 34 as seen in FIG. 5A in two, as shown by FIG. 5B.

The twofold combined web 28 is guided to a heat (or sonic) seal roll pair 143 by which the web 28 is formed with linear or ribbon-like heat seal zones 37 extending adjacent imaginary cutting lines 36 on opposite sides of the individual underpants 1 and thereby a continuous series of underpants 29 is formed.

The coninuous series of underpants 29 is guided by a guide roller 145 to a roll cutter 144 by which said continuous series of underpants is successively cut along the imaginary cutting lines 36 or at the heat seal zones 37 into the individual underpants 1 which are then transported by a belt conveyor 146 to a packagine process (not shown).

When a liquid impermeable web is employed as said continuous web 27 which is material of said backsheet 7 and it is desired to make at least the central zone of said backsheet at which said core 8 is disposed on said backsheet in order to avoid any possibility of body fluid leakage occuring therethrough said central zone, it is preferred to bond the liquid inpermeable web, preferably such web having elasticity made of plastic film or the like to the web 27 prior to placement of said elastic members 25A, 25B. In such a case, referring to FIG. 3, the web 27 is centrally applied with hot melt type adhesive in dotted pattern as the web 27 passes between a pressure roll 147 and an applicator roll 148 so that a liquid impermeable continuous web 40 may be bonded to said central zone. Accordingly, application of adhesive by said applicator station 102 as well as placement of the elastic members 25A, 25B are preformed, in this case, partially both on the web 40 and on the web 27.

Preferably, said webs 26, 27 are of nonwoven fabric which is elastic both in length and width or at least in width, said core 8 is made of fluffy pulp which was mixed with super-absorbent polymer powder and molded together, and said elastic members 24, 25A, 25B comprise natural or synthetic rubber strings or tapes, or plastic films presenting elasticity upon heat treatment. Said core 8 may be omitted depending on particular application of the underpants.

It should be understood that the step of FIG. 5A may be replaced by the step of FIG. 5B to cut out the central area 21' of said combined web 28 in forming said cutout 23 for the leg-hole. Furthermore, the adhesive zones 30a, 30b, 31, 32 may be applied with adhesive continuously extending overall on these zones, or in a plurality of dots, intermittent lines or helical lines.

What is claimed is:

1. A method for disposable underpants comprising steps of:

a) providing adhesive zones centrally on one side of a first continuous web intermittently along the length thereof;

b) introducing first and second continuous elastic members having a width narrower than that of a strip of adhesive defining said annular adhesive zones toward the central area on said one side, of said first continuous web so that said first continuous elastic member is laid to bond substantially along a half of said annular adhesive zone while said second continuous elastic member is laid to bond substantially along the remainder half of said annular adhesive zone;

c) providing adhesive zones extending along lateral edges on one side of at least one of said first continuous web and a second continuous web;

d) introducing third group of continuous elastic members between the mutually opposed sides of said first continuous web and said second continuous web along the respective lateral edges so as to be bonded between these webs along said adhesive zones;

e) bonding said first and second continuous webs together along said respective one sides to form a continuous combined web;

f) folding said continuous combined web into two along a longitudinally central line;

g) cutting off portions of said continuous combined web encircled within the respective annular zones each comprising said annular adhesive zone, said first and second elastic members bonded to the web along said annular adhesive zones, after forming or folding doube said combined web to form cutouts for leg-holes;

h) providing linear seal zones extending transversely of said folded continuous combined web centrally through said respective cutouts for the leg-holes to one lateral edge of said combined web corresponding to a waist line so as to form continuous series of underpants; and i) cutting said continuous series of underpants along each of said linear seal zones transversely of said continuous series of underpants so that each of said linear seal zones is divided in two longitudinally of said continuous combined web and thereby obtaining individual underpants.

2. The method for manufacturing disposable underpants as recited in claim 1, wherein, during or after said step "c", said second continuous web is provided on one side thereof with second annular adhesive zones to be aligned with the first-mentioned annular adhesive zones, respectively, and said second annular adhesive zones are bonded to said first and second continuous elastic members attached to said first annular adhesive zones.

3. The method for manufacturing disposable underpants as recited in claim 1, wherein said first and second continuous elastic members intersect each other at opposite ends of the respective annular adhesive zones as viewed longitudinally of said web.

4. The method for manufacturing disposable underpants as recited in claim 1, wherein an absorbent core is placed between each pair of adjacent said annular adhesive zones prior to combining said first and second continuous webs one upon another.

5. The method for manufacturing disposable underpants as recited in claim 1, wherein elastic fibrous nonwoven fabric is used as said first and second continuous webs.

6. The method for manufacturing disposable underpants as recited in claim 2, wherein said first and second continuous elastic members intersect each other at opposite ends of the respective annular adhesive zones as viewed longitudinally of said web.

7. The method for manufacturing disposable underpants as recited in claim 2, wherein an absorbent core is placed between each pair of adjacent said annular adhesive zones prior to combining said first and second continuous webs one upon another.

8. The method for manufacturing disposable underpants as recited in claim 2, wherein elastic fibrous nonwoven fabric is used as said first and second continuous webs.

9. A method for manufacturing disposable underpants comprising the steps of:

(a) providing a first continuous elongated web (27);

(b) establising a plurality of seperate annular adhesive zones (30a) each made up of an adhesive strip at spaced apart intervals along the length of said web (27);

(c) feeding both a first continuous elastic member (25a) and a second continuous elastic member (25b) toward said web (27) so that (1) said first continuous elastic member (25a) is deposited on approximately a first half of each annular adhesive zone (30a)

(2) said second continuous elastic member (25b) is deposited on approximately the second half of each adhesive zone (30a)

each of said elastic members (25a, 25b) having a width which is narrower than the width of the adhesive strip that makes up the annular adhesive zone (30a);

(d) providing a second continuous web (26);

(e) establishing adhesive zones (32) extending along lateral edges on one side of at least one of said webs (26,27);

(f) depositing a third group of continuous elastic members (24) into contact with said adhesive zones (32) set forth in (e);

(g) bonding said first and second webs (26,27) together so as to form a continuous combined web (28) with all of said elastic members (25a,25b,24) bonded therebetween;

(h) folding said continuous combined web (28) into two along a longitudinally central line (34);

(i) cutting off some portions of said continuous combined web (28) that are encircled within said annular adhesive zones (30a) either before or after step (h) so as to thereby form cutouts (23) for leg-holes;

(j) providing linear seal zones (37) transversely of said folded continuous combined web, said seal zones extending from about the center of said cutouts (23) for the leg-holes to the lateral edge of said combined web that corresponds to the waist line so as to form a continuous series of joined underpants; and (k) cutting said continuous series of joined underpants along each of said linear seal zones (37) transversely of said continuous series of underpants so that each of said linear seal zones (37) is divided in two longitudinally of said continuous combined web to thereby obtained individual underpants.

10. The method for manufactureing disposable underpants as recited in claim 9, wherein said second continuous web (26) is also provided on one side thereof with a plurality of spaced apart annular adhesive zones that are aligned with the annular adhesive zones of said first web (27) and said annular adhesive zones on said second web (26) are also bonded to said first and second continuous elastic members (25a,25b) attached to said first annular adhesive zones (30a).

11. The method for manufacturing disposable underpants as recited in claim 9, wherein the first and second continuous elastic members (25a, 25b) intersect each other on opposite sides of the annular adhesive zones as viewed longitudinally of said web.

12. The method for manufacturing disposable underpants as recited in claim 9, wherein an absorbent core (8) is placed between each pair of adjacent annular adhesive zones prior to step (g).

13. The method for manufacturing disposable underpants as recited in claim 9, wherein elastic fibrous nonwoven fabric is used as said first and second continuous webs.

14. The method for manufacturing disposable underpants as recited in claim 10, wherein said first and second continuous elastic members (25a, 25b) intersect each other on opposite sides of the annular adhesive zones as viewed longtudinally of said web.

15. The method for manufacturing disposable underpants as recited in claim 10, wherein an absorbent core (8) is placed between each pair of adjacent annular adhesive zones prior to step (g).

16. The method for manufacturing disposable underpants as recited in claim 10, wherein elastic fibrous nonwoven fabric is used as said first and second continuous webs.

17. A method according to claim 9, wherein step (c) said first and second elastic members (25a, 25b) are each deposited in a generally sinusoidal pattern.

18. A method according to claim 17, wherein the sinusoidal patterns cross over each other in the area between adjacent adhesive zones (30a).

19. A method according to claim 9, wherein in step (c) said first and second elastic members (25a,25b) are in a stretch condition at the time they are deposited on said annular adhesive zone (30a).

*20. In a method for manufacturing disposabe underpants, the step of applying the elastic comprising the steps of:*

*a. providing annular adhesive zones on one side of a first continuous web;*

*b. laying a tensioned first continuous elastic member in a first non-linear pattern to bond with at least a portion of at least one of said adhesive zones;*

*c. laying a second continuous elastic member in a second non-linear pattern to bond with at least a portion of said at least one of said adhesive zones, the first and second non-linear patterns being substantially symmetrically disposed about a longitudinally central line;*

*d. attaching said first continuous web to a second continuous web to form a continuous combined web; and*

*e. cutting off a central portion of said continuous combined web to form a web opening substantially surrounded by the first and second elastic members.*

*21. The method of claim 20, wherein said step of providing curvilinear adhesive zones include providing a plurality of oval adhesive zones on said first continuous web.*

*22. In a method for manufacturing disposable underpants, the step of applying the elastic comprising the steps of:*

*a. providing annular adhesive zones on one side of a first continuous web;*

*b. laying a tensioned first continuous elastic member in a first non-linear pattern to bond with at least a portion of at least one of said adhesive zones;*

*c. laying a second continuous elastic member in a second non-linear pattern to bond with at least a portion of said at least one of said adhesive zones, the first and second non-linear patterns being substantially symmetrically disposed about a longitudinally central line;*

*d. attaching said first continuous web to a second continuous web to form a continuous combined web; and*

*e. cutting off a central portion of said continuous combined web to form a web opening substantially surrounded by the first and second elastic members,*

*wherein said step of cutting off a central portion of said continuous combined web to form a web opening comprises the steps of:*

*i. folding said continuous combined web along a longtidinally central line; and*

*ii. cutting off portions of said continuous combined web encircled within said annular adhesive zones to form leg*-holes.

*23. The method of claim 22, wherein, after step (b) of claim 22, wherein the method includes the further steps of:*

*a. providing linear seal zones extending transversely across said folded continuous combined web at positions central to said leg-holes to form a continuous series of underpants; and*

*b. cutting said continuous series of underpants along each of said linear seal zones.*

*24. In a method for manufacturing disposable underpants, the step of applying the elastic comprising the steps of:*

*a. providing annular adhesive zones on one side of a first continuous web;*

*b. laying a tensioned first continuous elastic member in a first non-linear pattern to bond with at least a portion of at least one of said adhesive zone;*

*c. laying a second continuous elastic member in a second non-linear pattern to bond with at least a portion of said at least one of said adhesive zones, the first and second non-linear patterns being substantially symmetrically disposed about a longitudinally central line;*

*d. attaching said first continuous web to a second continuous web to form a continuous combined web; and*

*e. cutting off a central portion of said continuous combined web to form a web opening substantially surrounded by the first and second elastic members.*

* * * * *